US00PP17837P3

(12) United States Plant Patent
Cadic

(10) Patent No.: US PP17,837 P3
(45) Date of Patent: Jun. 26, 2007

(54) ***CARYOPTERIS* PLANT NAMED 'INOVERIS'**

(50) Latin Name: *Caryopteris×clandonensis*
Varietal Denomination: Inoveris

(75) Inventor: M. Alain Cadic, Beaucouze (FR)

(73) Assignee: Agri Obtentions S.A., Guyancourt Cedex (FR)

( * ) Notice: Subject to any disclaimer, the term of this patent is extended or adjusted under 35 U.S.C. 154(b) by 115 days.

(21) Appl. No.: 10/729,999

(22) Filed: Dec. 9, 2003

(65) Prior Publication Data

US 2004/0231020 P1 Nov. 18, 2004

Related U.S. Application Data

(63) Continuation of application No. 09/791,738, filed on Feb. 26, 2001, now abandoned.

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS

André Briant Jeunes Plants, Tarif Général, Saison 1999/2000 (Jul. 1999).

*Primary Examiner*—Kent Bell
*Assistant Examiner*—Annette H Para
(74) *Attorney, Agent, or Firm*—Buchanan Ingersoll & Rooney PC

(57) ABSTRACT

A new and distinct cultivar of *Caryopteris×clandonensis* plant is provided that is a seedling formed following the induced mutation of the 'Heavenly Blue' cultivar (U.S. Plant Pat. No. 1,091). Gamma radiation was utilized to create the mutation. The new cultivar can be readily distinguished from its parent by a more upright and more uniform growth habit, darker green foliage, more intense violet-blue flowers, and shorter internodes.

1 Drawing Sheet

Figure 1:
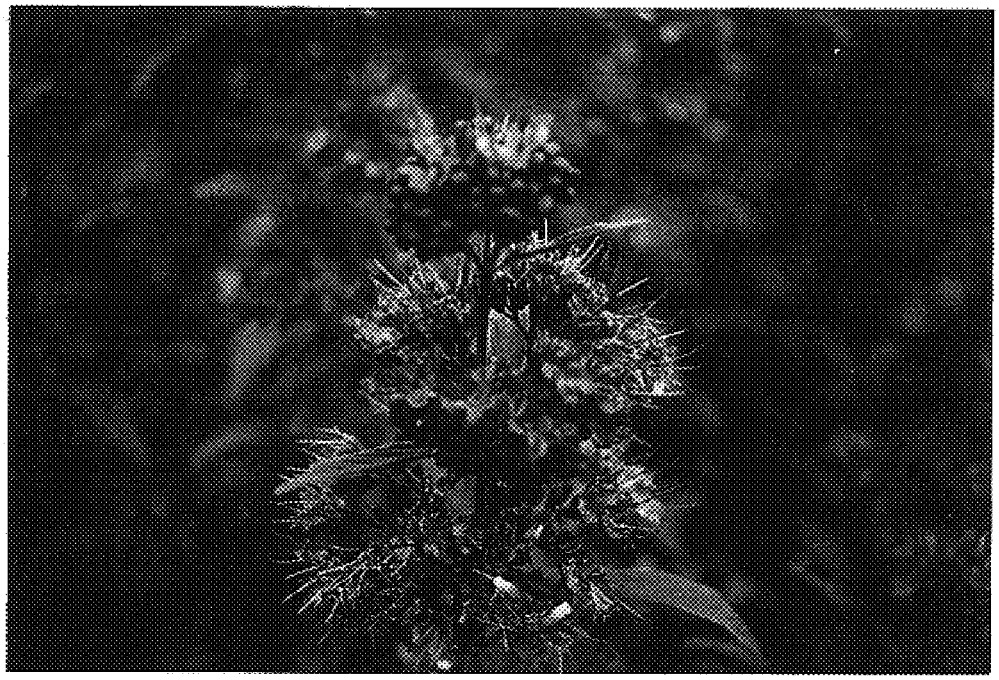

Botanical/commercial classification: *Caryopteris×clandonensis /Caryopteris* Plant.
Variety denomination: cv. 'Inoveris'.

SUMMARY OF THE INVENTION

A new and distinct cultivar of *Caryopteris×clandonensis* plant is provided. *Caryopteris* plants are generally recognized to be a hybrid of *Caryopteris incana×Caryopteris mongholica* and to be a better garden plant than either parent.

The new cultivar of the present invention is a mutation derived from the 'Heavenly Blue' cultivar (U.S. Plant Pat. No. 1,091). When creating the new cultivar, plants of the 'Heavenly Blue' cultivar were irradiated with cobalt gamma rays, seeds were formed thereon following self-pollination, and seedlings were produced upon planting which were observed and studied.

The irradiation and the study of the resulting seedlings were carried out at the Institut National De La Recherche Agronomique located at Angers, France.

It was found that a single plant observed following such irradiation and the planting of seeds possessed the characteristics of the *Caryopteris* cultivar of the present invention. The characteristics of such new cultivar can be summarized as follows when compared to the parent 'Heavenly Blue' cultivar:

(a) forms a more upright and more uniform growth habit,
(b) displays darker green foliage,
(c) forms in profusion attractive flowers that are a more intense violet-blue, and
(d) forms shorter internodes.

The new cultivar of the present invention well meets the needs of the horticultural industry, and is particularly well suited for growing as attractive ornamentation in the landscape. It can be treated as a perennial in the garden, and gives nice coloration in the garden during late summer.

As indicated hereafter, the new cultivar can be readily distinguished from its 'Heavenly Blue' parent.

Also, the new cultivar of the present invention can be readily distinguished from the 'Worcester Gold' cultivar (non-patented in the United States). For instance, the new cultivar exhibits a more compact growth habit, displays more uniform foliage that is less jagged than that of the 'Worcester Gold' cultivar, displays darker green foliage that can be contrasted to the golden foliage of the 'Worcester Gold' cultivar, and displays shorter styles than the 'Worcester Gold' cultivar.

The new cultivar has been found to readily undergo asexual propagation by the use of cuttings. Such asexual propagation has been carried out at Angers, France, and has confirmed that the characteristics are firmly fixed and are transmitted from one generation to another.

The new cultivar has been named the 'Inoveris' cultivar.

BRIEF DESCRIPTION OF THE PHOTOGRAPH

The accompanying photograph shows typical blossoms and foliage of the new variety. The depicted plant was approximately three years of age and was photographed on August 1st while growing outdoors at Angers, France. The attractive intense violet-blue blossoms and the nicely contrasting green foliage are illustrated.

DETAILED DESCRIPTION

The following description is based on the observation of plants of the new cultivar growing outdoors at Angers, France. Such plants had been asexually reproduced through the use of softwood cuttings and were approximately three years of age. The plants were initially grown in containers and were transplanted into the ground during the springtime where the soil was covered with polyethylene film. The soil tended to be low in organic matter and possessed a pH of approximately 6.5. Such soil tended to be wet in the winter and very dry during the summer. The color terminology utilized in the description that follows is to be accorded its ordinary dictionary significance. Reference to The R.H.S. Colour Chart of The Royal Horticultural Society, London, England, sometimes is included.

Origin: Seedling produced following the induced mutation of the 'Heavenly Blue' cultivar (U.S. Plant Pat. No. 1,091). The 'Heavenly Blue' cultivar was irradiated with gamma rays from cobalt 60.

Parentage: Seedling of 'Heavenly Blue'.

Plant:

*Form.*—Attractive flowering shrub.

*Habit.*—More upright and more uniform than the 'Heavenly Blue' cultivar. The habit is more regular and less random appearing than that of the 'Heavenly Blue' cultivar.

*Height.*—A mature plant commonly assumes a height of approximately 1 m at the end of the growing season.

*Width.*—A mature plant commonly assumes a width of approximately 75 cm at the end of the growing season.

*Internode length.*—Commonly approximately 3.7 cm on average, and shorter than those of the parent 'Heavenly Blue' cultivar.

*Configuration.*—Dense and taller than it is broad.

*Limbs.*—Possess a bright aspect.

Foliage:

*Disposition.*—Opposite.

*Texture.*—Smooth.

*Configuration.*—Lanceolate, the leaf tips are variable in shape and commonly are rounded-acuminate, and the leaf base is broad and wedge-shaped.

*Margins.*—Generally entire, but with a few teeth that appear at broad intervals.

*Color.*—Near Green Group 137A on the upper surface, near Greyed-Green Group 194A on the under surface, and darker than the 'Heavenly Blue' parent.

*Fragrance.*—When the leaves are crumpled they emit a strong fragrance resembling that of terpentine oil.

Inflorescence:

*Bearing.*—Borne in profusion in cymes as illustrated.

*Time of bearing.*—July to October at Angers, France.

*Buds.*—Initially are near Greyed-Green Group 189C in coloration, and with advancing maturity become a bicolored greyed-green and violet-blue in coloration.

*Corolla.*—Approximately 8 mm in length on average, possess a tube-like configuration at the base having a length of approximately 4 mm, and commonly three small rounded petals having a triangular configuration, a length of approximately 3 mm and a width of approximately 1.5 mm are present at the end of the tube together with a larger rounded petal having a fringed border that commonly measures approximately 4 mm×5 mm.

*Color.*—Dark violet-blue as illustrated, Violet-Blue Group 93A, with some lighting as the blossoms mature. The bloom coloration is more intense than that of the 'Heavenly Blue' cultivar.

*Sepals.*—Triangular in configuration, approximately 2 mm in length, and approximately 1 mm in width at the base.

*Stamens.*—Four per flower, and approximately 13.7 mm in length on average.

*Anthers.*—Near Violet-Blue Group 95B in coloration.

*Filaments.*—Near Violet-Blue Group 96D in coloration.

*Pistils.*—Extremely short in length and not readily measurable.

*Styles.*—Near Violet-Blue Group 96D in coloration.

*Ovaries.*—Near Yellow-Green Group 145A in coloration.

*Fruit.*—One per flower, and oval in shape prior to opening and possesses four compartments.

*Seeds.*—Flat and ellipsoidal with wings at the margins. The quantity of fruit is believed to be less than that produced by the 'Heavenly Blue' cultivar; however, no formal comparison has been undertaken.

Growing conditions: Does well in full to moderate sun, and prefers well-drained soil.

Hardiness: Plants have withstood −8° C. and have not been evaluated at cooler temperatures.

Insect resistance: No noticeable susceptibility to insects has been observed during observations to date.

Disease resistance: No noticeable susceptibility to disease has been observed during observations to date.

Propagation: Can be readily propagated while utilizing cuttings.

Usage: Provides attractive ornamentation when in bloom during late summer when few other woody plants bloom. Can be grown in the ground or in containers.

I claim:

1. A new and distinct cultivar of *Caryopteris*× *clandonensis* plant derived from the 'Heavenly Blue' cultivar (U.S. Plant Pat. No. 1,091) having the following combination of characteristics when compared to its 'Heavenly Blue' parent:

(a) forms a more upright and more uniform growth habit, (b) displays darker green foliage, (c) forms in profusion attractive flowers that are a more intense violet-blue, and (d) forms shorter internodes;

substantially as described and illustrated.

* * * * *